United States Patent [19]

Bruner, Jr. et al.

[11] Patent Number: 4,570,016

[45] Date of Patent: Feb. 11, 1986

[54] MANUFACTURE OF BUTANEDICARBOXYLIC ACID ESTERS

[75] Inventors: Harold S. Bruner, Jr., Hockessin; Michael B. D'Amore, Wilmington, both of Del.

[73] Assignee: E. I. Du Pont de nemours and Company, Wilmington, Del.

[21] Appl. No.: 660,179

[22] Filed: Oct. 12, 1984

[51] Int. Cl.³ .............................................. C07C 67/38
[52] U.S. Cl. .................... 560/204; 502/171; 502/201; 502/222; 502/229; 502/326
[58] Field of Search ............... 560/204; 502/171, 326, 502/222, 201, 229

[56] References Cited

U.S. PATENT DOCUMENTS

| | | | |
|---|---|---|---|
| 3,716,626 | 2/1973 | Kniese et al. | 423/418 |
| 4,007,130 | 2/1977 | Leach et al. | 252/411 R |
| 4,169,956 | 10/1979 | Kummer et al. | 560/204 |
| 4,171,451 | 10/1979 | Kummer et al. | 560/204 |
| 4,256,909 | 3/1981 | Kummer et al. | 560/204 |
| 4,258,203 | 3/1981 | Platz et al. | 560/204 |
| 4,281,173 | 7/1981 | Kesling | 560/204 |
| 4,310,686 | 1/1982 | Kummer et al. | 560/204 |
| 4,350,668 | 9/1982 | Isogai et al. | 423/139 |
| 4,421,692 | 12/1983 | Hofmann et al. | 260/410.9 R |

FOREIGN PATENT DOCUMENTS 2646955  4/1978  Fed. Rep. of Germany .
58-214345 12/1983  Japan .

Primary Examiner—Natalie Trousof
Assistant Examiner—Vera C. Clarke

[57] ABSTRACT

Deactivated cobalt catalyst from the carboxalkoxylation of butadiene is regenerated by contact with a strong acid ion exchange resin.

5 Claims, No Drawings

MANUFACTURE OF BUTANEDICARBOXYLIC ACID ESTERS

BACKGROUND OF THE INVENTION

1. Field of the Invention

This invention relates to the manufacture of butanedicarboxylic acid esters by the cobalt catalyzed carboalkoxylation of butadiene and, more particularly, to a process for regenerating the cobalt catalyst and recycling it to the reaction without extensive additional treatment.

2. Description of the Prior Art

The cobalt catalyzed carboalkoxylation of butadiene to produce dicarboxylic acid esters as the principal reaction products has been described in the literature. U.S. Pat. No. 4,169,956, issued on Oct. 2, 1979, describes a typical stepwise carbomethoxylation of butadiene initially to methylpentenoate and then to dimethyladipate. The patent discloses preparing catalyst by reacting an aqueous cobalt salt solution with excess carbon monoxide and hydrogen in the presence of activated charcoal followed by extracting the thus prepared catalyst with butadiene. The hydrocarbon solution containing the butadiene and cobalt carbonyl hydride is then reacted with carbon monoxide and an excess of an alkanol of 1-4 carbon atoms in the presence of a tertiary nitrogen base, e.g., pyridine. A portion of the base and excess hydrocarbon is then removed from the reaction product and the resultant mixture reacted with additional carbon monoxide and alkanol at elevated pressure. The unreacted alkanol and free tertiary nitrogen base are then separated from the reactants by distillation and the product which contains catalyst, butanedicarboxylic acid ester and byproducts is treated with an oxidizing agent in an aqueous acid medium. The acidic, oxidized reaction mixture is separated into an organic phase from which butanedicarboxylic acids are eventually isolated and an aqueous phase from which cobalt salts are eventually extracted with a water immiscible solvent. The resultant phase which contains the spent cobalt ($Co^{++}$) is then used to prepare fresh catalyst. The patentees further disclose that the cobalt salts obtained by extraction are advantageously treated in a strongly basic ion exchange apparently to remove any carboxylic acids present in the stream.

Another method for recovering cobalt catalyst from carboalkoxylations is described in U.S. Pat. No. 4,350,668, issued on Sept. 21, 1982 and involves the extraction of cobalt components from the reaction product with sufficient aqueous acid solution to react with all of the cobalt present. One preferred method for recovering the cobalt components from the extract involves neutralization of the extract with an alkaline solution to form cobalt hydroxide or basic cobalt carbonate which is precipitated from the solution. The cobalt salts are then recovered from the solids. The patentees also note that the reaction of acids with the tertiary amines must be avoided and for this reason their aqueous extraction process cannot be applied to the hydroesterification of butadiene in the presence of such amines.

A method of purifying carboxylic acid esters produced by reacting olefins with carbon monoxide and alkanols in the presence of a cobalt and pyridine-type catalyst is disclosed in U.S. Pat. No. 4,421,692, issued on Dec. 20, 1983, and involves the hydrogenation of the reaction mixture followed by treatment of the hydrogenate in an acid ion exchange to remove nitrogen compounds therefrom. The patentees teach that the sequence of treatment steps are critical and that the nitrogen contaminants are not sufficiently removed if the acid products are ion exchanged prior to hydrogenation.

The recycle of the reaction products from the preparation of alkylpentenoates is disclosed in U.S. Pat. No. 4,256,909, issued on Mar. 17, 1981. Variations in the reaction conditions employed for the carboalkoxylation are disclosed in U.S. Pat. Nos. 4,171,451, issued on Oct. 16, 1979; 4,310,686, issued on Jan. 12, 1982 and 4,258,203, issued on Mar. 24, 1981.

SUMMARY OF THE INVENTION

A process for the preparation of dialkylbutanedicarboxylic acid esters which comprises reacting butadiene or a hydrocarbon mixture containing butadiene alone or in combination with other olefins and/or the partial carboalkoxylation products of butadiene with carbon monoxide and a lower alkyl alcohol, e.g., methanol, ethanol, etc. in the presence of a cobalt carbonyl catalyst and a tertiary nitrogen base, e.g., pyridine, at elevated temperature and pressure. The reaction product, or at least a portion thereof, optionally with adjustment of the composition, e.g., removal of unreacted materials such as butadiene by distillation or the extraction of the ester product is passed through an acidic cation exchange resin whereupon the deactivated cobalt catalyst is regenerated to a condition satisfactory for a direct recycle to the reaction.

One embodiment of the process of the present invention employs alkyl alcohols having 2-8 carbon atoms to suppress the deactivation of the cobalt carbonyltertiary nitrogen base promoted catalyst.

DETAILED DESCRIPTION OF THE INVENTION

The carboalkoxylation reaction is advantageously conducted in a plurality of steps or stages initially involving the reaction of butadiene to form the alkylpentenoate and then the reaction of the pentenoate to form the dialkyladipate.

In the first step butadiene is reacted with carbon monoxide and a lower alkyl alcohol having 1-4 carbon atoms, e.g., methanol, at a temperature in the range 80°-150° C. and a pressure in the range 100-2000 atmospheres in the presence of a cobalt-containing catalyst, e.g., cobalt octacarbonyl and a nitrogen base. Generally, the reactants are maintained in a mole ratio of cobalt to nitrogen base to butadiene to alcohol of 1 to 5-30 to 8-25 to 10-30, respectively, while maintaining proper stoichiometry. The mole ratio of cobalt to the nitrogen base is preferably maintained in the range 7-20. The principal products of the initial step are the partially alkoxylated butadiene, e.g., methyl 3-pentenoate.

After removal of residual butadiene and adjustment of the amount of nitrogen base to within the limits set forth below, the reaction product from the first step can be employed in the second step without additional treatment. However, it is within the purview of the present invention that other materials can be added to or removed from the reaction product from the first step before it is sent to the second step. Optionally, all, or a portion of, the catalyst which is deactivated in the first step can be regenerated according to the process of the present invention before reacting the pentenoate. The conditions employed in the second step are similar to those employed in the initial step except that the temperature is higher, e.g., 140°-200° C. and the amount of nitrogen base is lower, e.g., the mole ratio of cobalt to nitrogen base is maintained in the range 2–10 and preferably 3–8.

The catalyst employed in the carboalkoxylation is a cobalt carbonyl compound preferably in combination with a tertiary nitrogen base. Sources of cobalt include finely divided metallic cobalt, inorganic salts such as cobalt nitrate or carbonate, organic salts, in particular carboxylates. Cobalt carbonyl or hydrocarbonyls can likewise be employed; dicobalt octacarbonyl is very suitable. Typically the cobalt-containing catalyst is prepared for the first step by dissolving a cobalt compound [typically as $Co_2(CO)_8$] in the nitrogen base and alcohol at room temperature under a nitrogen blanket. Catalyst can be added for the second step as the cobalt salt of an organic acid, e.g., cobalt acetate. In both instances the active catalyst forms in situ.

The tertiary nitrogen bases which are employed as promoters for the cobalt comprise N-heterocyclic compounds with 5–11 carbon atoms and a pKa in the range 4–8, preferably 5–7, and include, but are not necessarily limited to, pyridine (pKa 5.3), alkylpyridines, e.g., 3-picoline (pKa 6.0) and isoquinoline (pKa 5.4). Pyridine is the preferred nitrogen-containing base.

The ion exchange resin serves a dual purpose of removing the N-methylpyridinium ion (catalyst deactivation product) from the process while regenerating the catalyst by replacing the lost acidity either as protons or, in the presence of excess amine, as the amine-proton adduct. Any strong acid ion exchange resin including any of the known polymers in the macroporous or gel form which contain strongly acidic functional groups such as styrene-divinylbenzene copolymers substituted with sulfonic or phosphonic acid functional groups, particularly those macroporous resins sold under the trade names "Amberlyst 15" and "Dowex MSC-1" and gel resins sold under the trade names "Amberlite 118", "Duolite ES 26" and "Dowex HCR-S" are operable. Resins of formaldehyde condensation polymers substituted with sulfonic acid groups, e.g., "Duolite C-3" are also useful. Considerations common in ion exchange technology, e.g., holdup time, temperature, capacity of resin and concentration of species to be removed are applicable to this process. The ion exchange resin can be reactivated by contact with aqueous acid and the nitrogen base recovered from the eluent.

The regeneration can be partial or essentially complete and can be applied to carboalkoxylation after the initial step and the partially or fully regenerated catalyst can be recycled to the first step or passed to the second step without adjustment of the composition of the reaction product. If it is desired to remove a portion of the reactants or products, this should be done before ion-exchange to minimize the volume of material passed through the resin. The regeneration can also be performed after the preparation of the dialkyladipate by treating all or a portion of the product stream, usually after removal of the adipate and associated esters, etc. and the regenerated catalyst can be recycled to either or both of the reaction steps.

In one preferred embodiment, butadiene, carbon monoxide, methanol and pyridine are introduced into the initial reaction along with regenerated catalyst. Excess butadiene and pyridine are removed from the product from the first reactor following which additional methanol and catalyst is combined therewith and the resultant product is directed to a second reactor. The product from the second reactor is contacted with 0.01–0.05 parts of water per part of product and the resulting solution is extracted with a hydrocarbon such as cyclohexane, pentane, hexane and/or heptane to recover the ester product, e.g., dimethyladipate, before the organic phase is directed to the ion exchange.

The following examples are presented to illustrate but not to restrict the present invention. Parts and percentages are by weight unless otherwise noted.

EXAMPLE 1

In order to demonstrate the effectiveness of ion exchange in regenerating cobalt catalyst for the carboalkoxylation of butadiene, N-methylpyridinium tetracarbonyl cobaltate which represents the spent catalyst resulting from the carboalkoxylation reaction was prepared by heating $Co_2(CO)_8$, methanol, pyridine in a ratio of 1:8:4 at 175° C. for 4 hours under 2500 psig of CO.

Approximately 10.5 parts of the catalyst prepared as described above was dissolved in 10 parts of acetone, and passed over 35 parts of a strong acid, macroreticular ion exchange resin comprising sulfonic acid on partially crosslinked polystyrene sold under the trade name "Amberlyst 15" which was converted to free acid form using 1N HCl. The solution was passed through the resin at a rate of 4 parts by volume of solution per volume of resin per minute using 4 bed volumes of methanol as a carrier to assure complete catalyst recovery. The eluent was evaporated to dryness under vacuum at 65° C. and the residue analyzed by Nuclear Magnetic Resonance which showed approximately 60% removal of the N-methylpyridinium ion. This residue was again dissolved in methanol and exchanged over the same resin and under the same conditions to assure essentially complete removal of the N-methylpyridinium ion. After evaporating the second residue to dryness, approximately six parts of the residue (red oil) was combined with 53.6 parts of methanol, 40.5 parts of butadiene and 6.9 parts of pyridine. This mixture was heated at 130° C. for 5 hours under a pressure of 5000 psig of carbon monoxide following which the product was cooled to room temperature and the carbon monoxide vented. By analysis the product contained methyl 3-pentenoate in a yield of 83% formed at the rate of 0.0090 l per mole of cobalt per minute.

COMPARATIVE 1

In order to demonstrate that the regenerated catalyst, according to the process of Example 1, is equivalent with freshly prepared catalyst approximately 7.40 parts of cobalt octacarbonyl was prepared by dissolving the cobalt complex in 19 parts each of methanol and pyridine under a nitrogen atmosphere at room temperature. This solution was combined with 35 parts of methanol, 43.4 parts of butadiene and 50 parts of pyridine and the mixture heated at a temperature of 130° C. under 5000 psig pressure of carbon monoxide for 5 hours following which the product was cooled to room temperature and the carbon monoxide vented. The analysis of the product indicated a yield of 87% to methyl 3-pentenoate at a rate of 0.0085 l per mole of cobalt per minute.

COMPARATIVE 2

Approximately 12.9 parts of the catalyst prepared as initially described in Example 1 was combined with 53.6 parts of methanol, 43.1 parts of butadiene and 68.9 parts of pyridine. This mixture was heated at a temperature of 130° C. under a pressure of 5000 psig carbon monoxide for a period of 5 hours following which the product was cooled to room temperature, the carbon monoxide vented and the product analyzed. The yield to methyl 3-pentenoate was approximately 18% at a rate of 0.00072 l per mole of cobalt per minute. The foregoing in conjunction with Example 1 demonstrates the superior result obtained using the regeneration technique of the present invention.

EXAMPLE 2

Approximately 224 parts of methyl 3-pentenoate, 120 parts of methanol, 40 parts of pyridine and 14.8 parts of $Co_2(CO)_8$ were mixed at 175° C. and 2500 psig CO pressure for 5 hours following which the product was cooled to room temperature and the carbon monoxide vented. Analysis of the product indicated a yield of dimethyladipate of 77% at an 85% conversion of methyl 3-pentenoate. Polarographic analysis of this product showed that essentially all of the cobalt was present as the inactive N-methylpyridinium tetracarbonylcobaltate.

To approximately 100 parts of the above product were added 1 part of water to promote phase separation and the resultant product was shaken with 140 parts of cyclohexane while under a nitrogen atmosphere. The phases were separated and the heavier polar phase (containing 99+% of the cobalt) was stripped under 2 mm Hg vacuum at room temperature to remove water. The remaining liquid was then treated with fresh pyridine to increase the pyridine to cobalt ratio to 20.

A resin in acid form was prepared by alternately slurrying and filtering 100 parts of "Amberlyst 118″″" with 500 parts of 1N NaOH and 1N HCl, 3 times each. After one additional HCl treatment, the resin was slurried twice with 400 parts of methanol to remove water and then presaturated with pyridine by thoroughly contacting the resin with a solution containing 100 parts cyclohexane, 50 parts methanol, 50 parts methyl acetate, 50 methyl valerate, 100 parts pyridine, 570 parts dimethyladipate and 30 parts water to simulate a typical product.

The thus prepared resin (100 parts) was then slurried with 160 parts of the liquid prepared as above (pyridine/cobalt molar ratio 20/1) which represents a typical spent catalyst. After about 5 minutes mixing under a nitrogen blanket at room temperature, the resin and liquid were separated by filtration. A solution was prepared by combining 120 parts of the filtrate, 60 parts of methanol and 23.5 parts of butadiene and then was heated at 130° C. and 5000 psig CO pressure for 5 hours. Analysis for methyl 3-pentenoate indicated an 85% yield with a formation rate constant of 0.035 l/mole of cobalt per minute.

EXAMPLE 3

A carbomethoxylation reaction was conducted by combining under nitrogen 202 parts of methanol, 75.4 parts of pyridine, 360 parts of methyl 3-pentenoate and 34 parts of anhydrous cobalt acetate in a shaker bomb; pressuring the bomb to 2160 psig with carbon monoxide; and then heating the contents for 10 hours at 170° C. The reaction products were then cooled to room temperature and the carbon monoxide vented.

Approximately 450 parts of the product from the above-described carbomethoxylation was contacted with 15 parts of water and then extracted with 970 parts of cyclohexane under a nitrogen blanket. The phases were separated and the polar phase which contained essentially all of the catalyst and residual methanol impurities along with a minor percentage of the dimethylester was analyzed by differential pulse polarograph which showed that essentially all of the catalyst was present as the inactive N-methylpyridinium tetracarbonylcobaltate. Approximately 40 parts of this material were passed over 35 parts of the strong acid ion exchange resin prepared as described in Example 2 at the rate of 4 ml/min using 200 parts of methanol as a carrier. Analysis of the exchanged material indicated approximately 75% regeneration of the catalyst.

We claim:

1. A process for the preparation of dialkyl butanedicarboxylic acid esters which comprises initially reacting a mixture comprising a compound selected from the class consisting of butadiene, carboalkoxylation products of butadiene and mixtures of the foregoing with carbon monoxide and a lower alkyl alcohol in the presence of a cobalt-containing catalyst and tertiary nitrogen base at temperatures in the range 80°–200° C. and pressures in the range 100–2000 atmospheres to obtain a reaction product, contacting at least a portion of the reaction product with a strongly acidic ion exchange resin and returning at least a portion of the thus treated material to the initial reaction.

2. The process of claim 1 wherein the tertiary nitrogen base is pyridine.

3. The process of claim 1 wherein the strongly acid ion exchange resin comprises a styrene-divinylbenzene copolymer substituted with sulfonic acid groups.

4. The process of claim 3 wherein the tertiary nitrogen base is pyridine.

5. The process of claim 4 wherein the lower alkyl alcohol is methanol.

* * * * *